United States Patent
Javid et al.

(10) Patent No.: US 10,098,867 B2
(45) Date of Patent: Oct. 16, 2018

(54) USE OF PHYTOCANNABINOIDS IN THE TREATMENT OF OVARIAN CARCINOMA

(71) Applicant: GW Research Limited, Histon, Cambridge, Cambridgeshire (GB)

(72) Inventors: Farideh Afshin Javid, Huddersfield (GB); Marnie Duncan, Cambridge (GB); Colin Stott, Cambridge (GB)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 14/899,613

(22) PCT Filed: Jun. 19, 2014

(86) PCT No.: PCT/GB2014/051889
§ 371 (c)(1),
(2) Date: Dec. 18, 2015

(87) PCT Pub. No.: WO2014/202990
PCT Pub. Date: Dec. 24, 2014

(65) Prior Publication Data
US 2016/0136128 A1    May 19, 2016

(30) Foreign Application Priority Data

Jun. 19, 2013 (GB) .................................. 1310910.3
Apr. 10, 2014 (GB) .................................. 1406473.7

(51) Int. Cl.
| | |
|---|---|
| *A61K 31/352* | (2006.01) |
| *A61K 45/06* | (2006.01) |
| *A61K 31/05* | (2006.01) |
| *A61K 31/192* | (2006.01) |
| *A61K 31/353* | (2006.01) |
| *A61K 36/185* | (2006.01) |

(52) U.S. Cl.
CPC ............. *A61K 31/352* (2013.01); *A61K 31/05* (2013.01); *A61K 31/192* (2013.01); *A61K 31/353* (2013.01); *A61K 36/185* (2013.01); *A61K 45/06* (2013.01)

(58) Field of Classification Search
None
See application file for complete search history.

(56) References Cited

FOREIGN PATENT DOCUMENTS

| | | |
|---|---|---|
| EP | 2 044 935 A1 | 4/2009 |
| GB | 2 450 493 A | 12/2008 |
| GB | 2 478 595 A | 9/2011 |
| WO | WO 2008/144475 A1 | 11/2008 |
| WO | WO 2013/038157 A1 | 3/2013 |

OTHER PUBLICATIONS

Afaq et al., Cannabinoid receptors as a target for therapy of ovarian cancer. Proc Amer Assoc Cancer Res. Apr. 2006;66(8): Abstract 4615.
Holland et al., Interaction of plant cannabinoids with the multidrug transporter ABCC1 (MRP1). Eur J Pharmacol. Sep. 4, 2008;591(1-3):128-31. doi: 10.1016/j.ejphar.2008.06.079.
Schindl et al., Level of Id-1 protein expression correlates with poor differentiation, enhanced malignant potential, and more aggressive clinical behavior of epithelial ovarian tumors. Clin Cancer Res. Feb. 2003;9(2):779-85.
Torres, The Data is Very Strong: Marijuana Plant Extract Stops Cancers From Spreading. Sep. 28, 2012. Retrieved from <http://preventdisease.com/news/12/092812_Marijuana-Plant-Extract-Stops-Cancers-From-Spreading.shtml > on Nov. 4, 2016.

*Primary Examiner* — Gigi Georgiana Huang
(74) *Attorney, Agent, or Firm* — Wolf, Greenfield & Sacks, P.C.

(57) ABSTRACT

The present invention relates to the use of phytocannabinoids in the treatment of ovarian cancer. Preferably the phytocannabinoid is selected from the group consisting of: cannabidiol (CBD); cannabidiol acid (CBDA); cannabigerol (CBG); cannabigerolic acid (CBGA); cannabigerol propyl variant (CBGV); and tetrahydrocannabivarin (THCV). In a further embodiment the one or more phytocannabinoids are used in combination with each other. Preferably the combination of cannabinoids consists of CBD and CBG.

3 Claims, No Drawings

# USE OF PHYTOCANNABINOIDS IN THE TREATMENT OF OVARIAN CARCINOMA

RELATED APPLICATION

This application is a national stage filing under 35 U.S.C. § 371 of international application PCT/GB2014/051889, filed Jun. 19, 2014, which was published under PCT Article 21(2) in English, the disclosure of which is incorporated by reference herein in its entirety.

The present invention relates to the use of phytocannabinoids in the treatment of ovarian cancer. Preferably the phytocannabinoid is selected from the group consisting of: cannabidiol (CBD); cannabidiol acid (CBDA); cannabigerol (CBG); cannabigerolic acid (CBGA); cannabigerol propyl variant (CBGV); and tetrahydrocannabivarin (THCV). In a further embodiment the one or more phytocannabinoids are used in combination with each other.

BACKGROUND TO THE INVENTION

Ovarian cancers arise due to the uncontrollable division of abnormal cells in the ovary. The resultant tumour can be benign or malignant. Benign tumours will not spread to other parts of the body, however malignant tumours often do. Cancerous tumours may spread to nearby structures such as the uterus or fallopian tubes and if the cancer remains undetected or untreated the malignant cells will then spread further to the bowel, liver or lungs.

Ovarian cancer is one of the major causes of cancer-related death in women. Additionally it is the most common gynaecologic type of cancer. Even though there is relatively low incidence of this type of cancer, ovarian cancer has a high fatality ratio, with overall 5-year survival of less than 30%.

Cancer of the ovary affects more than 6,500 women in the UK each year. It is the fifth most common cancer among women after breast cancer, bowel cancer, lung cancer and cancer of the uterus (womb).

Ovarian cancer is often diagnosed at a late stage as the symptoms, such as persistent bloating, pain in the pelvis and lower stomach and difficulty eating are similar to other conditions.

Because ovarian cancer is often diagnosed at an advanced stage (3 or 4) when it has spread to other parts of the abdomen. Advanced cancer may not be curable. The goal of treatment is to put the tumour into remission so it shrinks or disappears.

Surgery may be used to remove as much of the cancer as possible, in addition chemotherapy or radiotherapy may be used to reduce symptoms such as pain by shrinking the cancer.

Chemotherapy involves the use of cytotoxic drugs to kill cancer cells. It is often given after surgery for ovarian cancer. In some cases, it can be given before surgery as it may help shrink the tumour and make it easier to remove.

Several different drugs can be used in chemotherapy. Often, a combination is given. The most common treatment for ovarian cancer is a carboplatin, which is used alone or in combination with another drug, paclitaxel.

Over the course of the chemotherapy, different tests can monitor how the ovarian cancer is responding to treatment. The level of CA125 in your blood may be increased in a patient with ovarian cancer and blood tests can be used to see if the level of this chemical is falling. In addition the tumour may be visible on a CT or ultrasound scan, repeated scans can be used to see whether it has shrunk.

The main side effects of chemotherapy are caused by its influence on normal, healthy cells, such as immune cells. Side effects include: infections; loss of appetite, nausea and vomiting, tiredness, hair loss and sore mouth.

At present, there are inadequate treatment options for the management of ovarian cancer, and therefore development of novel approaches for treatment of this disease are needed.

Surprisingly the applicant has discovered that certain phytocannabinoids are able to produce apotosis of ovarian carcinoma cells. Additionally combinations of phytocannabinoids are able to significantly reduce the ovarian cancer cells viability.

BRIEF SUMMARY OF THE DISCLOSURE

In accordance with a first aspect of the present invention there is provided the use of one or more phytocannabinoids in the treatment of ovarian cancer.

Preferably the phytocannabinoid is selected from the group consisting of: cannabidiol (CBD); cannabidiol acid (CBDA); cannabigerol (CBG); cannabigerolic acid (CBGA); cannabigerol propyl variant (CBGV); and tetrahydrocannabivarin (THCV).

More preferably the phytocannabinoid is CBG.

In a further embodiment the one or more phytocannabinoids are used in combination with each other.

Preferably the combination of phytocannabinoids is CBD in combination with CBG.

Alternatively the combination of phytocannabinoids is CBD in combination with THCV.

Preferably the phytocannabinoids are in the form of an extract or botanical drug substance.

Alternatively the phytocannabinoids are in an isolated or pure form.

In accordance with a second aspect of the present invention there is provided a composition for use in the treatment of ovarian cancer comprising one or more phytocannabinoids.

Preferably the phytocannabinoid is selected from the group consisting of: cannabidiol (CBD); cannabidiol acid (CBDA); cannabigerol (CBG); cannabigerolic acid (CBGA); cannabigerol propyl variant (CBGV); and tetrahydrocannabivarin (THCV).

In this specification the following terms are used and are intended to have the following meanings/definitions:

"Cannabinoids" are a group of compounds including the endocannabinoids, the phytocannabinoids and those which are neither endocannabinoids nor phytocannabinoids, hereafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and SR141716 (rimonabant).

An "isolated phytocannabinoid" is one which has been extracted from the cannabis plant and purified to such an extent that all the additional components such as secondary and minor cannabinoids and the non-cannabinoid fraction have been removed.

A "synthetic cannabinoid" is one which has been produced by chemical synthesis this term includes modifying an isolated phytocannabinoid, by for example forming a pharmaceutically acceptable salt thereof.

A "botanical drug substance" or "BDS" is defined in the Guidance for Industry Botanical Drug Products Guidance, June 2004, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of cannabis, BDS derived from cannabis plants do not include highly purified Pharmacopoeial grade cannabinoids The structure of the phytocannabinoids, CBD, CBDA, CBG, CBGA, CBGV and THCV are as shown below:

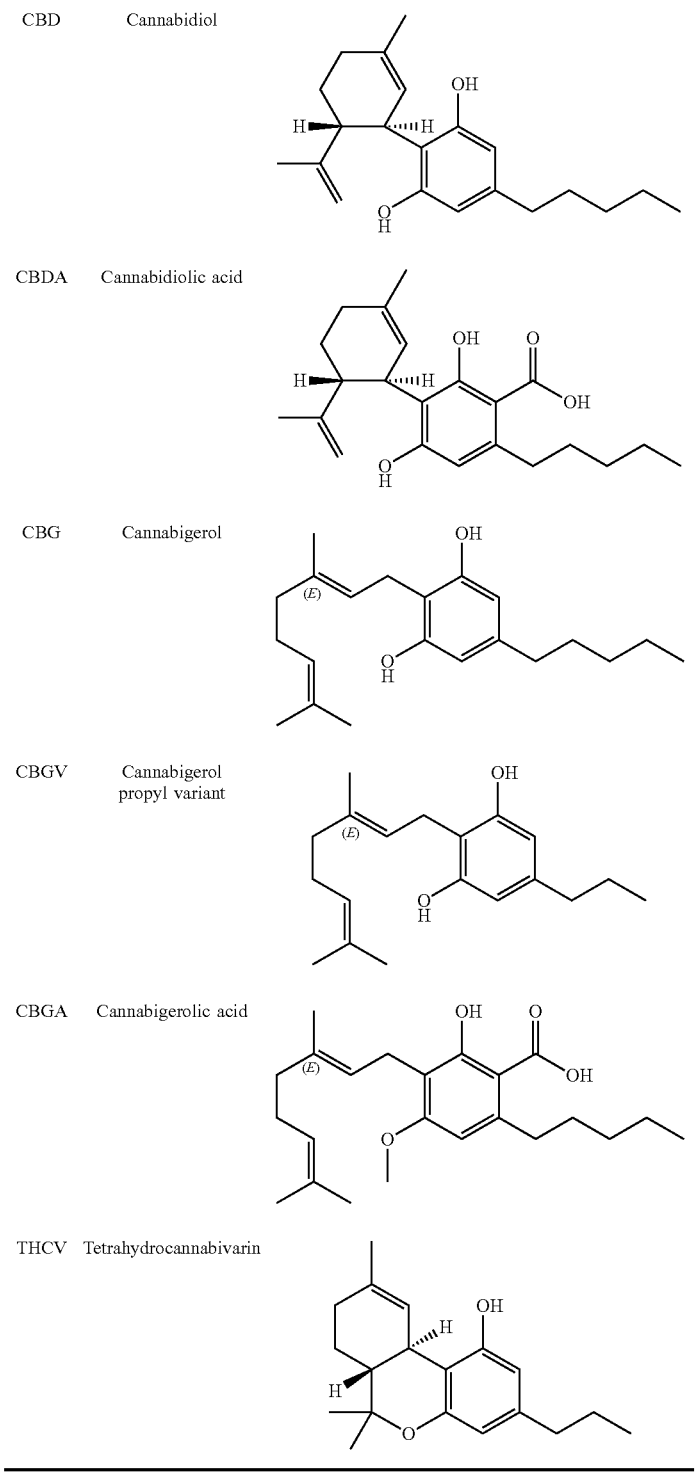

DETAILED DESCRIPTION

The Example below demonstrates the effects of different phytocannabinoids on the growth of ovarian carcinoma cells.

In addition Example 2 demonstrates the effect of combinations of phytocannabinoids.

EXAMPLE 1

Effect of Phytocannabinoids on Ovarian Carcinoma Cells

Materials and Methods

An ovarian carcinoma cell line, A2780 was grown and maintained in RPMI 1640 medium supplemented with 10% fetal bovine serum at 37° C., 5% $CO_2$. The cells were plated in 96-well culture plates at a density of $1\times10^4$ cells/well and allowed to adhere at 37° C. for 24 hours.

The cells were starved with 1% serum overnight, then treated with various concentrations of different phytocannabinoid (1 nm-100 mM) for various incubation periods.

The different phytocannabinoids tested were: cannabidiol (CBD); cannabidiol acid (CBDA); cannabigerol (CBG); cannabigerolic acid (CBGA); cannabigerol propyl variant (CBGV); and tetrahydrocannabivarin (THCV).

A cell viability assay, MTT, was performed following four different incubation times of 24 hours, 48 hours, 72 hours and 96 hours.

The supernatant was removed and MTT (3-(4,5-dimethylthiazol-2-yl)-2,5-diphenyltetrazolium bromide) was added for 4 hours. The ability of cells to form formazan crystals by active mitochondrial respiration was determined by using a Microplate reader after dissolving the crystals in DMSO.

Cytotoxicity was expressed as a relative percentage of the absorbance measured at 540 nm in the control and drug-treated cells. IC50 values were also calculated.

In all experiments data were presented as the mean and analysed using ANOVA followed by Dunnet's t-test; n=4.

Results

Table 1 below describes the IC50 values for the different phytocannabinoids at the four different time points used in the study.

TABLE 1

| IC50 values for the phytocannabinoids tested | | | | |
|---|---|---|---|---|
| | IC50 value (µM) | | | |
| Phytoannabinoid | 24 hours | 48 hours | 72 hours | 96 hours |
| CBD | 0.98 | 0.95 | 1.90 | 3.63 |
| CBDA | 16.00 | 9.50 | 10.00 | 11.80 |
| CBG | 2.00 | 0.83 | 0.85 | 3.38 |
| CBGA | 12.50 | 9.90 | 9.25 | No data |
| CBGV | 6.00 | 3.50 | 4.00 | No data |
| THCV | 8.00 | 5.75 | 8.75 | 9.00 |

The data above shows that all of the phytocannabinoids tested reduced the number of ovarian cancer cells present to a greater or lesser degree.

At a time point of 24 hours after the cannabinoids were added both CBG and CBD are shown to be very potent with both having lower IC50 values than the other phytocannabinoids tested. After 48 hours CBG becomes marginally more potent than CBD with the greatest effect shown after 72 hours.

Conclusion

Both CBD and CBG are good candidates for use in the treatment of ovarian cancer.

EXAMPLE 2

Effect of Combinations of Phytocannabinoids on Ovarian Carcinoma Cells

Materials and Methods

An ovarian carcinoma cell line, A2780 was grown and maintained in RPMI 1640 medium supplemented with 10% fetal bovine serum at 37° C., 5% $CO_2$. The cells were plated in 96-well culture plates at a density of $1\times10^4$ cells/well and allowed to adhere at 37° C. for 24 hours.

The different phytocannabinoid combinations that were tested were: A: cannabidiol (CBD) in combination with tetrahydrocannabivarin (THCV) and B: CBD in combination with cannabigerol (CBG).

The cells were starved with 1% serum overnight. In Experiment A various doses of CBD (1 nM-10 µM) were tested in the absence or presence of 1 hours pre-treatment of THCV (1 µM) for various incubation periods. In Experiment B various doses of CBD (1 nM-10 µM) were tested in the absence or presence of CBG (1 nM-100 µM) for various incubation periods.

A cell viability assay, MTT, was performed following four different incubation times of 24 hours, 48 hours (CBG combination only), 72 hours and 96 hours.

The supernatant was removed and MTT (3-(4,5-dimethylthiazol-2-yl)-2,5-diphenyltetrazolium bromide) was added for 4 hours. The ability of cells to form formazan crystals by active mitochondrial respiration was determined by using a Microplate reader after dissolving the crystals in DMSO.

Cytotoxicity was expressed as a relative percentage of the absorbance measured at 540 nm in the control and drug-treated cells. IC50 values were also calculated.

In all experiments data were presented as the mean and analysed using ANOVA followed by Dunnet's t-test; n=4.

Results

Table 2 below describes the IC50 values for the combination of THCV and CBD at the three different time points used in the study.

TABLE 2

| IC50 values for the phytocannabinoids tested | | | |
|---|---|---|---|
| | IC50 value (µM) | | |
| Phytocannabinoid | 24 hours | 72 hours | 96 hours |
| CBD | 12.50 | 5.87 | 5.62 |
| THCV | 16.25 | 14.75 | 10.50 |
| CBD + THCV | 9.13 | 0.03 | 0.006 |

As can be seen by Table 2 above co-treatment with THCV significantly reduced the cytotoxicity induced by CBD.

Table 3 below describes the IC50 values for the combination of CBG and CBD at the four different time points used in the study.

TABLE 3

IC50 values for the phytocannabinoids tested

| Phytocannabinoid | IC50 value (µM) | | | |
|---|---|---|---|---|
| | 24 hours | 48 hours | 72 hours | 96 hours |
| CBD | 11.79 | 6.85 | 7.92 | 4.43 |
| CBG | 13.94 | 9.48 | 9.96 | 8.96 |
| CBD + CBG | 8.28 | 4.03 | 4.13 | 1.35 |

As can be seen by Table 3 above the combination of CBD and CBG significantly decreases the IC50 values of the compounds on their own.

Conclusion

Combinations of phytocannabinoids are good candidates for use in the treatment of ovarian cancer.

The invention claimed is:

1. A method for treatment of ovarian cancer comprising administering to a patient with ovarian cancer a combination of cannabidiol (CBD) and cannabigerol (CBG).

2. The method as claimed in claim 1, wherein the CBD and CBG are in the form of an extract or botanical drug substance.

3. The method as claimed in claim 1, wherein the CBD and CBG are in an isolated form.

* * * * *